United States Patent

Bartz

[11] 4,345,912
[45] Aug. 24, 1982

[54] URANIUM PROSPECTING BASED ON SELENIUM AND MOLYBDENUM

[75] Inventor: Gerald L. Bartz, Amarillo, Tex.

[73] Assignee: Phillips Petroleum Company, Bartlesville, Okla.

[21] Appl. No.: 186,780

[22] Filed: Sep. 12, 1980

[51] Int. Cl.³ .................................... G01N 33/24
[52] U.S. Cl. .................................... 23/230 EP
[58] Field of Search .............. 23/230 EP, 230 R; 73/151, 153

[56] References Cited

U.S. PATENT DOCUMENTS

| | | |
|---|---|---|
| 2,183,964 | 12/1939 | Horvitz ........................ 23/230 EP |
| 2,367,592 | 1/1945 | McDermott ................... 23/230 EP |
| 2,370,793 | 3/1945 | Horvitz ........................ 23/230 EP |
| 2,725,281 | 11/1955 | Bond ............................. 23/230 EP |
| 2,949,339 | 8/1960 | Marvin . |
| 3,100,681 | 8/1963 | Townend et al. . |
| 3,180,703 | 4/1965 | Ableson et al. . |
| 3,223,476 | 12/1965 | Hart . |
| 4,067,693 | 1/1978 | Wimberley ................... 23/230 EP |

*Primary Examiner*—Ronald Serwin

[57] ABSTRACT

The ratio of extrinsic selenium and extrinsic molybdenum of a formation sample is used to characterize the area from which the sample has been taken as an exterior or an interior area of the formation with respect to a uraniferous roll-front location.

3 Claims, 6 Drawing Figures

URANIUM PROSPECTING BASED ON SELENIUM AND MOLYBDENUM

BACKGROUND OF THE INVENTION

This invention relates to a geochemical method of determining the location and shape of a uranium ore body. More specifically, the invention relates to determining the direction of offset drilling during the operation to define the uranium reserves of a roll-front type uranium deposit.

Uranium ore grade within a roll-front deposit is not uniform. Therefore, to evaluate the uranium reserves and plan an effective mining program, the distribution of ore grade must be delineated from gamma-ray data generated within bore holes which intersect the ore body. In plan view the roll-front assumes a sinuous pattern. Because of this shape the majority of the bore holes drilled in a reserve assessment program intersect the host sand either in the interior, behind the roll-front (updip) or in the exterior, in front of the roll-front (downdip) sediments associated with a roll-front body. When diagnostic characteristics of the interior or exterior sediments, i.e., color, gamma-ray configuration, are not definitive, the direction of offset is the result of geologic intuition. As a result, many holes may be offset in the wrong direction at high and wasted expenses.

The most commonly used technique of differentiating interior from exterior sediments is based on the color of the host sand. Within an actively migrating ore body the interior sands occur updip from the ore. Interior sands are buff colored, reflecting the dominance of ferric iron in the sediment. Uranium accumulates immediately downdip from the interface (also called the redox boundary) between the interior sediments and the exterior sediments. Exterior sands are grey in color, reflecting the dominance of ferrous iron. Thus during a reserve evaluation program, if the drill cuttings from the hosts and are buff in color, the next hole is offset downdip from the hole. Conversely, if the drill cuttings are grey, the next hole is offset updip.

The above method is simple and fast and requires no special training. However color of host sand cannot be used to discriminate the interior from exterior sands in all uranium deposits. For example basin tectonics, which occur following the emplacement of an ore body can superimpose reducing groundwaters upon the oxidizing sands. Consequently the color of the interior sand changes from buff to grey and the ore body is surrounded by grey sand. Another example such as a geologically rapid uplift, may cause a precipitous drop in the water table and strand an ore body. As a result the ore bodies are surrounded by buff sands.

Petrographic techniques of discerning interior from exterior sediments also exist. The techniques are based on the presence of certain mineral assemblages that retain their diagnostic integrity even after reducing conditions are superimposed upon the interior sediments. These minerals are not unique to a uranium deposit and several within the suite may occur in any aquifer which has a redox boundary. Thus drill cuttings from an overlying, non-uraniferous stratus can contaminate the sample and result in an erroneous classification of the sediment. In addition the sample must be examined shortly after collection or be dried and stored in a chemically and biologically inert environment to prevent changes in the mineral assemblage. This method also requires a relatively large amount of sample, 50 grams.

THE INVENTION

It is thus one object of this invention to provide a uranium prospecting method by which the area of a formation can be readily characterized as being exterior or interior with respect to a uraniferous body.

Another object of this invention is to provide for a uranium prospecting process which is simple and can be used on relatively small samples.

Yet another object of this invention is to provide for a process which allows the accurate and reliable planning of offset drillings to determine the shape and location of a uranium ore body.

These and other objects, advantages, details, features and embodiments of this invention will become apparent to those skilled in the art from the following detailed description of the invention, the appended claims and the drawing.

Figure 1:
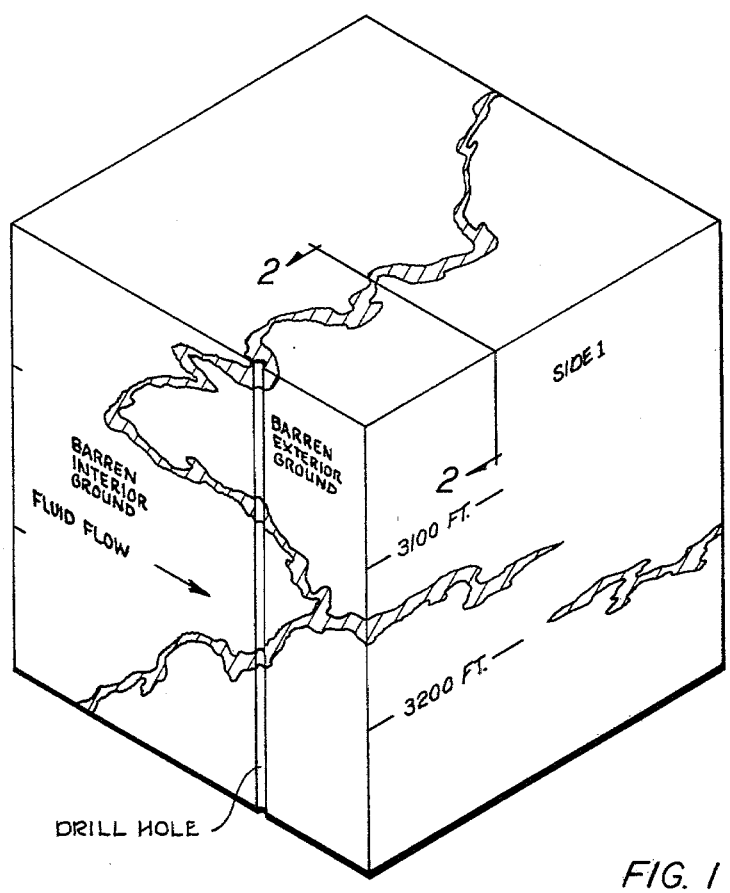
FIG. 1 is a three-dimensional cross sectional view of strata showing a uranium roll-front and a drill hole therethrough.

In accordance with this invention a method is proposed wherein the ratio of extrinsic selenium and extrinsic molybdenum of a sample of a formation is determined for characterizing this formation.

The method proposed allows characterization of interior and exterior formation material from the ratio derived from the extrinsic content of selenium and molybdenum. The process does not suffer from the shortcomings of the known method. The method is applicable to uranium ore deposits surrounded by grey sediments. The elements analyzed are preferentially concentrated in uranium deposits and significant concentrations of the elements are seldom found in overlying barren sediments so that contamination of the samples is significantly reduced. The method is not applicable to oxidized uranium deposits. Furthermore, normal sample handling does not affect the concentration ratio of the elements selenium and molybdenum. The method uses small samples in the size of e.g. 2–4 grams.

Although this method was used in a uranium roll-front complex surrounded by reduced sand the method is applicable to conventional roll-front deposits which contain oxidized interior sands and reduced exterior sands. The Se/Mo ratio will not work in the oxidized uranium deposits because they contain negligible amounts of molybdenum.

Finally, this method is applicable to a uranium deposit whether it be primary, detrital or epigenetic, in which there is evidence to infer that a portion of uranium was leached by oxidizing groundwater either prior, during or after the formation of the ore body.

It is not implied that the method described to extract or determine the extrinsic content is the most efficient or effective method. Different extraction and/or analytical techniques may result in different ratios and a different success ratio in predicting the correct direction of offset drilling.

The proposed method is based on the geochemical behavior of selenium, molybdenum and uranium. All three elements:

(1) are concentrated in the tuffaceous-rich sediment and granitic rocks believed by most workers knowledgeable in the field to be the source of the uranium deposits.

(2) are leached from the source rock and transported by alkaline to near-neutral groundwaters and (3) are deposited at or near a redox boundary.

The method for determining extrinsic selenium in formation samples is a process that dissolves only the surface matter of the sample.

This process can be briefly described as follows: Drill cutting or core sample is ground to fine mesh such as 200 mesh. The ground material is acid digested in a mineral acid such as hydrochloric (HCl), sulfuric ($H_2SO_4$), or nitric ($HNO_3$) for a time sufficient to digest the grain surface material but short enough to leave the interior of the grain sample intact. The resulting liquid is then analyzed using an atomic absorption analyzer for selenium, one such analyzer being manufactured by Perkin-Elmer.

The process for determining the extrinsic molybdenum is similar to the process for determining the extrinsic selenium and can be broadly described as follows. Drill cutting or core sample is ground to a fine mesh and then pressed into a pellet and analyzed directly using X-ray fluorescence with this method being good to a few parts per million. Another method that doesn't divert from the invention would be the use of plasma emission analyzing techniques. The analyzing techniques are known to those skilled in the art. The selenium and molybdenum concentrations of these analyses are used in the ratio of the invention.

A method for determining lower concentrations of extrinsic molybdenum is carried out as follows:

A core sample is ground into a fine mesh particle size, such as 200 mesh. The ground material is acid digested in a mineral acid such as hydrochloric, sulfuric, or nitric for a time sufficient to dissolve the grain surface matter but short enough to leave the core intact. The resulting liquid is analyzed for extrinsic molybdenum using the atomic absorption technique.

In connection with this invention, reference is frequently made to the ratio of extrinsic selenium to extrinsic molybdenum. The ratio of extrinsic molybdenum to extrinsic selenium can also be determined which is the reciprocal value of the former. The information obtained from such an analysis is the same and it is intended that this invention encompasses both methods. For simplicity reasons in the following reference will be usually made to only one of these ratios.

The order of deposition of the elements relative to the redox boundary is:

(1) maximum selenium concentration in the interior sediments lying immediately updip from the redox boundary.

(2) maximum uranium concentrates in the grey sediments lying immediately downdip from the redox boundary and (3) maximum molybdenum concentration in the exterior sediments lying immediately downdip from the uranium maximum.

This sequential order of deposition has been reported in several major districts of the United States. The samples for this information were collected from the walls of mines and not as drill cuttings. However, the dispersion halos of selenium and molybdenum associated with the ore deposit did not extend an appreciable distance from the ore bodies. In fact, the halos are so small that anomalous concentrations of selenium and molybdenum cannot be detected if the bore hole misses the ore body by 150 feet or more. These halos are areas into which the minerals of interest have moved by diffusion caused by their anomalously high concentration.

This size limitation of the halo may reflect the analytical method. The selenium and molybdenum concentration reported were the total concentrations of these elements in the sample. The total is the sum of the matrix (background) content of that element and the extrinsic content of that element, i.e. that portion deposited by the fluids which deposited the ore body. The small halo reflects the fact that small concentrations of the extrinsic content are masked by background variations in matrix material. For example the background content of selenium in sandy sediments is 2–5 ppm. If the actual matrix content of sample were 2 ppm, it would require in excess of 3 ppm of extrinsic selenium to classify this sample as an anomaly. In the sediments studies thus far, the anomaly halo for selenium as defined by the 3 ppm isoval is significantly smaller than 0.2 ppm extrinsic selenium isoval which surrounds the ore body.

The geochemical technique proposed is the chemical analysis of drill cuttings for their extrinsic content of selenium and molybdenum. Interior sediments have a Se/Mo ratio equal to the value determined as a result of known location analysis or, as in one case, equal to or greater than unity and frequently contain no detectable extrinsic molybdenum. Exterior sediments, within one horizontal mile of an ore body, are enriched in extrinsic molybdenum relative to extrinsic selenium, and consequently have a Se/Mo ratio, as determined by known location analysis, or as in the mentioned case, less than unity. This method was used in several problem areas on the fringe of the major ore body. The fringe areas contained weaker mineralization, a greater degree of discordance of the ore body and smaller ore bodies than the area in which the characteristics ratios were obtained. Preliminary evaluation of this geochemical method indicates that the method correctly predicted the direction of offset drilling in 37 out of 41 cases.

A further advantage of this method is that sampling does not involve special treatment of the sample to stabilize the diagnostic characteristics of the interior of exterior sediments.

Another advantage of this method is not that the effects of sample contamination is minimal to non-detectable. Iron-bearing contaminants are not distinguishable from those in the ore bearing unit and these contain matrix selenium. Drill cutting commonly contains shale and sand from overlying non-uraniferous strata. No time-effective method has been found to separate the shale contaminant. However, extrinsic selenium and molybdenum have not been detected in the contaminating shale and barren sands contain no detectable molybdenum and have less than 0.1 ppm of extrinsic selenium.

The extrinsic molybdenum content is a potential indicator of relative distance of the bore hole from the ore body. The extrinsic molybdenum content is a potential indicator of the relative ore grade between regions. In the exterior sediments the concentration of extrinsic molybdenum is greater (3-200) in the exterior sediments of richer ore bodies than the concentration (3-30 ppm) in sediment similarly distributed about a body of poorer grade.

The dispersion halo of the extrinsic concentration of elements associated with a roll-front deposit are larger than those created from the total concentration of the element and not associated with a roll-front; because of the magnitude of the dispersion halo the extrinsic content of selenium and molybdenum or ratios derived thereof is useful within certain phases of exploration. Included also are concentrations of compounds of these elements as formulated from the extrinsic content and ratios derived therefrom.

It is not implied that the size of the dispersion halo of extrinsic elements is similar for all uranium deposits.

The offset drilling proposed is implemented preferably in the following manner:

In an area which contains a rich ore body and in which the characteristic indicators of the interior, ore body and exterior sediments are known, a pattern of bore holes is implemented which intersect the ore body and extend approximately one mile on either side of the body. Horizontal distance between bore holes within this area should be 100 feet within the ore body and 200 feet within barren sediments.

From these bore holes drill cuttings are collected at set intervals from known uranium bearing stata and those suspected of containing uranium. A sample interval of ten vertical feet has proved successful in the areas situated.

A representative sample, approximately 2-4 grams, of each interval collected is analyzed for the extrinsic selenium and molybdenum content and determine the Se/Mo ratio of each sample using the before described extraction technique.

The samples are categorized into interior and exterior sediments based on the value of the selenium to molybdenum ratio as compared to the ratio value from known location tests, and the characteristic range of Se/Mo for each group is noted.

Drilling second bore holes responsive to the characterization of said primary sample ratios and characterizing said second bore hole samples such as to determine location and shape of a uranium ore body is carried out.

Figure 2:
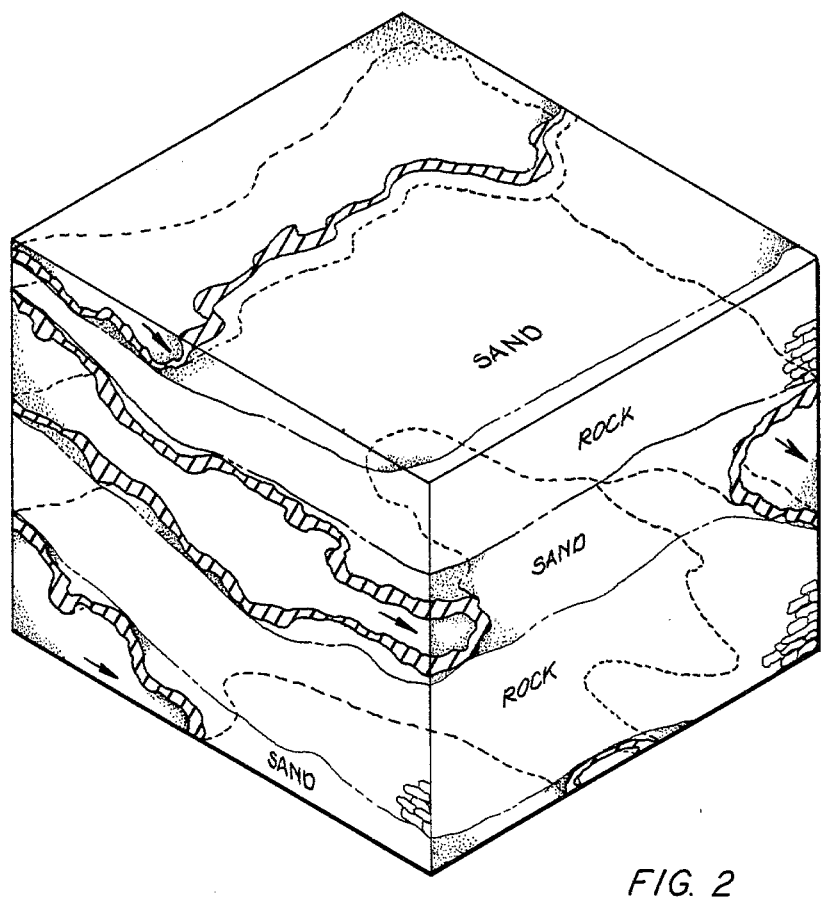
FIG. 2 is a three-dimensional cross section of the uranium roll-front along lines 2—2 of FIG. 1.

As seen in FIGS. 1 and 2, a three dimensional representation of an ore body which is hatched, a bore hole drilled in a strata intersects either the ore body or the host sand updip or downdip from the ore body.

Figure 3:
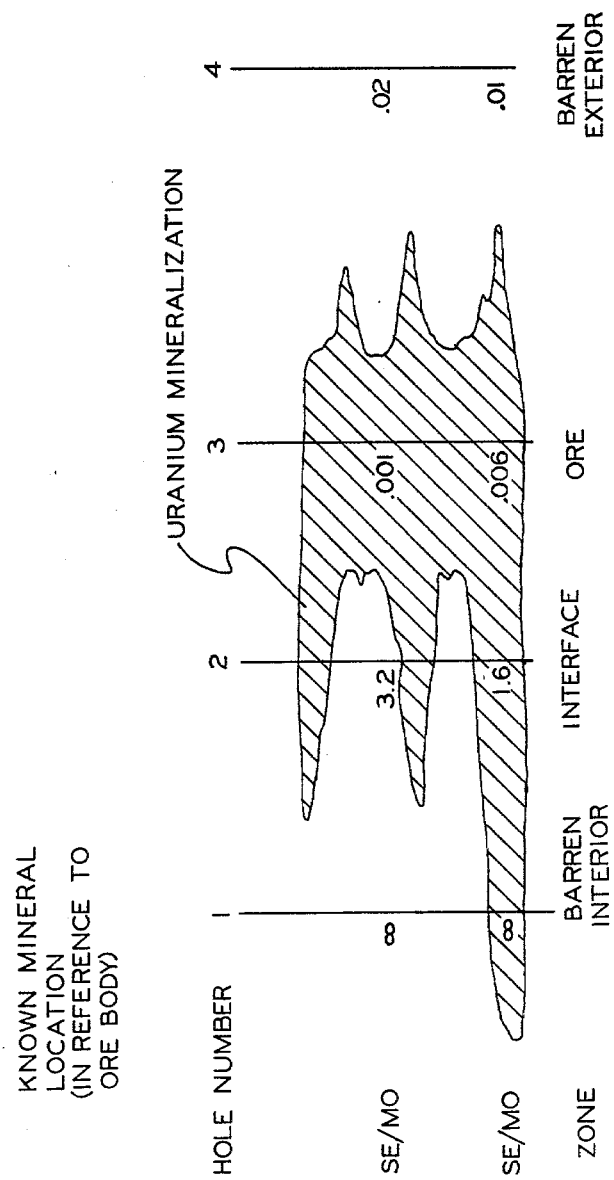
FIG. 3 is a two-dimensional cross sectional view through a formation with four bore holes and an ore deposit.

FIG. 3 shows the determination of the selenium in excess in the interior and molybdenum in excess in the exterior. The hole locations in reference to the roll-front is known and the range of the ratio value that indicates interior versus exterior sediment is determined. In this example, a selenium to molybdenum ratio less than 0.1 indicates the sample is located in the ore body or downdip. A value greater than or equal to 0.1 indicates the sample is located updip of the ore body. Only two Se/Mo ratios are shown for each hole, indicating representative range of the ratio over the holes depth. The ore body is indicated by the shaded area.

Figure 4:
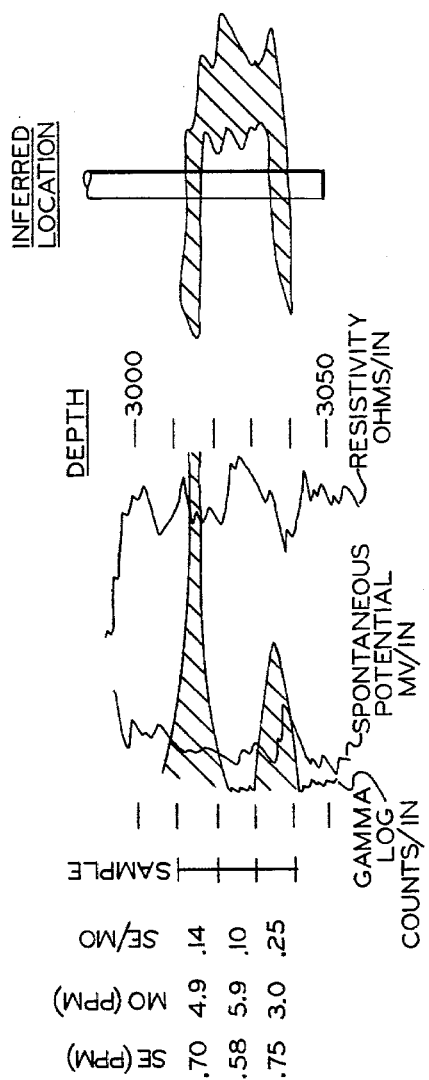
FIGS. 4, 5 and 6 are two dimensional cross sectional views of three bores holes showing the corresponding ratios and electric logs in conjunction with the inferred location of the ore body in reference to said bore holes.
Figure 5:
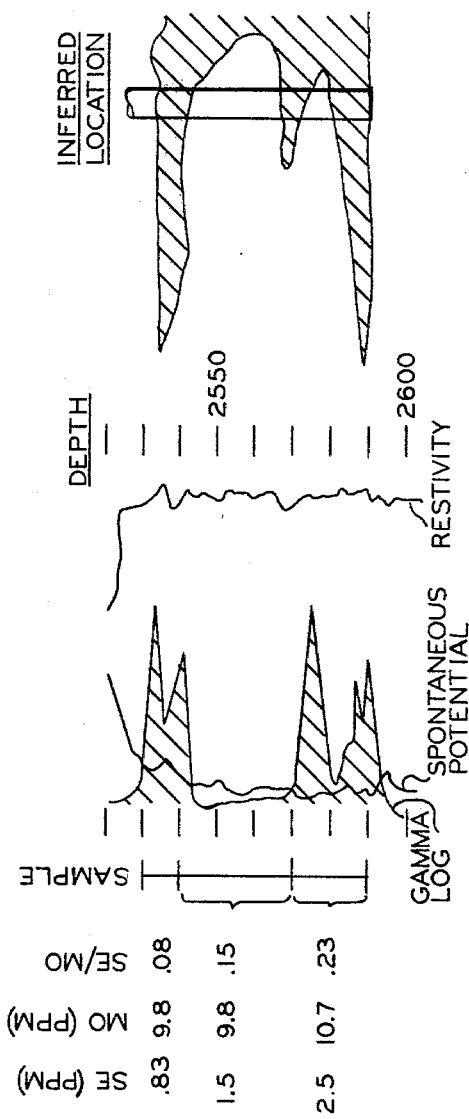
Figure 6:
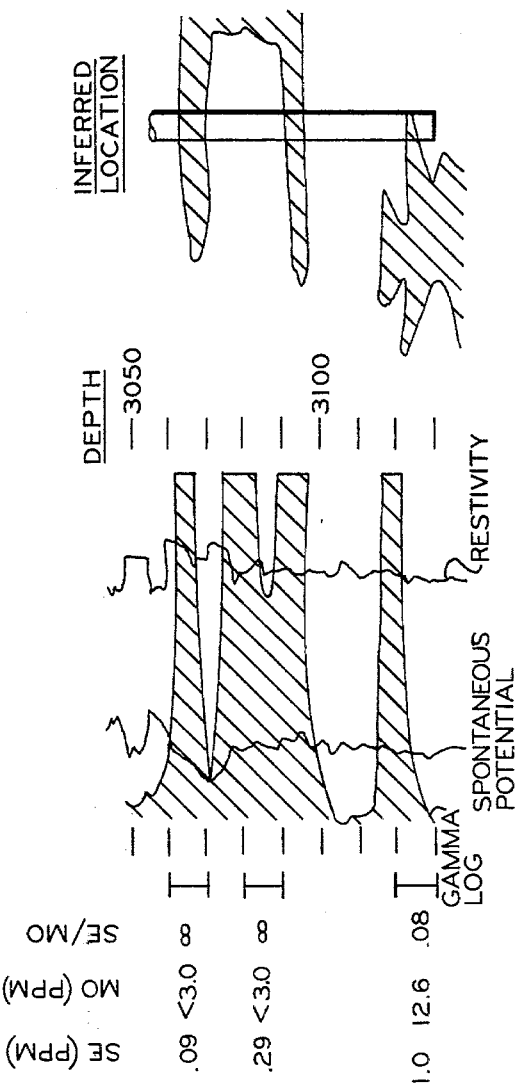

FIGS. 4, 5 and 6 show the selenium/molybdenum analyzed data, electric log data, and inferred location of uranium to depth of three bore holes. The inferred location of the ore body in reference to the drill hole is determined by the value of said ratio in conjunction with the electric logs, gamma log in particular. For example, in FIG. 4, the 3010-3020 foot depth selenium to molybdenum ratio predicts an updip location, however the gamma log indicates an ore body. The ratio is near the interior to exterior break over value and thus would place greater confidence in said reading to be an ore body. A similar situation is also seen in FIGS. 5 and 6. Most drilling operations utilize a plurality of sampling and logging techniques which are compared for a final evaluation.

Reasonable variations and modifications which will become apparent to those skilled in the art can be made in this invention without departing from the spirit and scope thereof.

I claim:

1. Uranium prospecting process useful for non-oxidized uranium deposits comprising
   a. drilling one or more first holes through a formation,
   b. obtaining at least one first sample of the formation material from said first hole or holes from a known depth in the formation,
   c. determining the ratio of extrinsic selenium to extrinsic molybdenum of said sample, relating the location from which said sample had been taken as exterior or interior by categorizing said samples into interior and exterior samples based on the value of said ratio as compared to the ratio value from known location tests, the terms "extrinsic selenium" and "extrinsic molybdenum" referring to the content of selenium or molybdenum in the surface matter of the sample particles; and
   d. determining from said information obtained in step c. the location and/or shape of a uranium ore body.

2. A process in accordance with claim 1 wherein said process is used in an area wherein the boundaries of a uranium ore body are generally known and said drilling and analyzing is carried out to provide detailed information on said ore body by drilling said first holes within roughly 1 mile of the known boundaries of said ore body.

3. A process in accordance with claim 2 wherein the distance between bore holes is about 50 to about 150 feet for bore holes within the ore body and about 150-300 feet in formation bordering said ore body.

* * * * *